United States Patent [19]

Izumi

[11] Patent Number: 4,635,631
[45] Date of Patent: Jan. 13, 1987

[54] ARTIFICIAL RESPIRATION VENTILATOR OF AIR CONSTANT FLOW

[75] Inventor: Kazuo Izumi, Osaka, Japan

[73] Assignee: Sharp Kabushiki Kaisha, Osaka, Japan

[21] Appl. No.: 666,248

[22] Filed: Oct. 29, 1984

[30] Foreign Application Priority Data

Nov. 4, 1983 [JP] Japan .............................. 58-207973

[51] Int. Cl.$^4$ ........................................... A61M 16/00
[52] U.S. Cl. ................................................ 128/204.23
[58] Field of Search ..................... 128/204.21, 204.23, 128/204.24, 204.25

[56] References Cited

U.S. PATENT DOCUMENTS

| | | | |
|---|---|---|---|
| 2,830,579 | 4/1958 | Saklad et al. | 128/204.23 |
| 3,741,208 | 6/1973 | Jonsson et al. | 128/204.21 |
| 3,961,627 | 6/1976 | Ernst et al. | 128/204.21 |
| 4,323,064 | 4/1982 | Hoenig et al. | 128/204.21 |

Primary Examiner—Henry J. Recla
Attorney, Agent, or Firm—Birch, Stewart, Kolasch and Birch

[57] ABSTRACT

A respiratory circuit for an artificial inspiration ventilator is characterized in that it controls a volume of an O2/air constant flow as being substantially reversely proportional to a positive and negative airway pressures by patient's own respiration. The respiratory circuit comprises a pressure sensor for detecting an inner pressure of the respiratory circuit, a comparator for comparing the inner pressure with reference values prescribed by reference voltages, and a switching circuit responsive to the results of the comparator for switching a valve passing the O2/air constant flow.

3 Claims, 2 Drawing Figures

ARTIFICIAL RESPIRATION VENTILATOR OF AIR CONSTANT FLOW

BACKGROUND OF THE INVENTION

The present invention relates to a ventilator and, more particularly, to an artificial respiration ventilator for constant air flow from an inspiration inlet to an expiration outlet in a respiratory circuit.

Conventionally, there is an artificial respiration ventilator with a type of intermittent assist ventilation and continuous positive airway pressure ventilation. A constant flow of air has been provided from an inspiration inlet to an expiration outlet of a respiratory circuit that includes a patient's lungs. In the conventional type, however, no care is taken to continuously compensate for the amount of air involved in the patient's own respiration,.

SUMMARY OF THE INVENTION

Accordingly, it is an object of the present invention to provide an improved artificial respiration ventilator for changing a continuous air flow to a patient's lungs.

It is another object of the present invention to provide an improved artificial respiration ventilator for continuously providing an air volume to compensate for a change of an inner pressure of a respiratory circuit according to a patient's own respiration.

It is a further object of the present invention to provide an improved respiratory circuit for an artificial respiration ventilator so as to change a continuous air volume so as to compensate for a patient's own respiration.

Briefly described, in accordance with the present invention, a respiratory circuit for an artificial respiration ventilator is characterized in that it controls a volume of a constant O2/air flow as being substantially inversely proportional to a positive and negative airway pressures from a patient's own respiration. The respiratory circuit comprises pressure sensor means for detecting an inner pressure of the respiratory circuit, comparator means for comparing the inner pressure with reference values prescribed by voltages, and switching means responsive to the results of the comparator means for switching a valve that passes the constant O2/air flow.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE INVENTION

Figure 1:
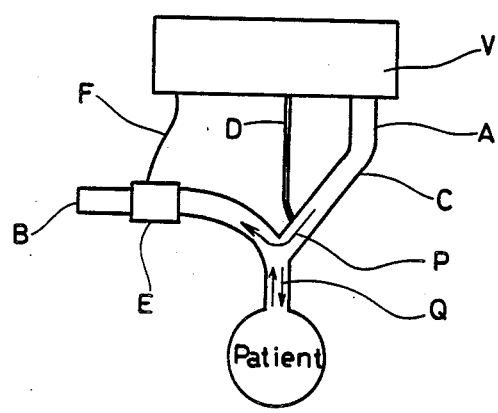
FIG. 1 is a schematic configuration of an artificial respiration ventilator according to the present invention.

FIG. 1 is a schematic configuration of an artificial respiration ventilator according to the present invention.

The artificial respiration ventilator of FIG. 1 comprises a ventilator body V, and a respiratory circuit C attached to the body V. The circuit C extended between an inspiration inlet A and an exhaustion outlet B includes a branch for turning a constant flow P to a patient's own respiration side Q, and a tube D for forwarding an inner pressure of the respiratory circuit C into a pressure sensor of the ventilation body V. At the expiration side of the respiratory circuit C, an expiration valve E is provided for increasing a positive end expiration airway pressure referred to as PEEP. The valve E is coupled to an expiration valve controller via a line F.

In the preferred embodiment of the present invention, when a negative airway pressure is caused in the respiratory circuit C, the volume of the constant flow P is increased and when the positive airway pressure of the circuit C exceeds a predetermined value, the volume of the constant flow P is decreased.

Figure 2:
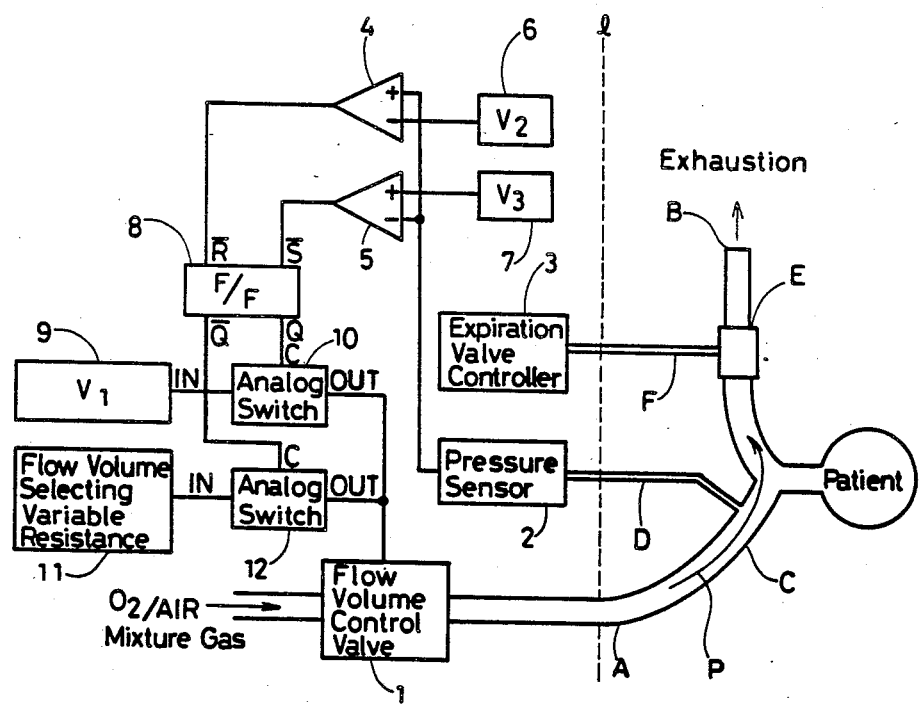
FIG. 2 is a block diagram of a respiratory circuit in the ventilator of FIG. 1.

FIG. 2 is a block diagram of the respiratory circuit C of FIG. 1. Like elements corresponding to those of FIG. 1 as positioned at the right side of a broken line 1 are denoted by like symbols.

Referring to FIG. 2, a flow volume control valve 1 is provided for opening a valve in direct proportion to an inputted voltage value, so that as the inputted voltage value is larger, an opening degree of this valve is larger. Through the opening of this valve, air containing O2 can pass into the respiratory circuit C. A pressure sensor 2 serves to detect the inner pressure of the respiratory circuit C and develop a corresponding an output voltage. An expiration valve controller 3 acts to open an expiration valve E during the constant flow condition. A pair of comparators 4 and 5 are provided which are electrically coupled to the pressure sensor 2 and a second voltage setter 6, and the sensor 2 and a third voltage setter 7, respectively. The comparator 4 serves to compare a pressure value of the pressure sensor 2 with a pressure corresponding to a second set voltage V2 of the voltage setter 6. The comparator 5 serves to compare the pressure value of the pressure sensor 2 with a pressure corresponding to a third set voltage V3 of the voltage setter 7.

A flip/flop 8 is coupled to the pair of the comparators 4 and 5 in such a manner that an output terminal of the comparator 5 is connected to a SET terminal of the flip/flop 8 while an output terminal of the comparator 5 is coupled to a RESET terminal of the flip/flop 8.

An output Q of the flip/flop 8 is inputted into an analog switch 10 connected to a first voltage setter 9 setting a first voltage V1. Another output $\overline{Q}$ of the flip/flop 8 is inputted into an analog switch 12 connected to a flow volume selecting variable resistance 11 comprising a variable resistance variably selecting an output pressure. Therefore, the analog switches 10 and 12 serve to switch on and off the flow volume control valve 1 and either the first voltage setter 9 or the flow volume selecting variable resistance 11, respectively. When the Q output of the flip/flop 8 is high, namely, "1" as represented by "c" in FIG. 2, the analog switch 10 become closed to conduct the IN terminal with the OUT terminal thereof. While the first voltage V1 of the first voltage setter 9 is applied to the flow volume control valve 1 and when the $\overline{Q}$ of the flip/flop 8 is changed to be high "1" as represented by "c", the analog switch 12 becomes closed to conduct the IN terminal and the OUT terminal so that a voltage set by the flow volume selecting variable resistance 11 is applied into the flow volume control valve 1.

According to the present invention, the constant flow volume during an inspiration is selected by the voltage across the variable resistance. While the patient inspirates during the flowing of the constant flow in the respiratory circuit C, the flip/flop 8 is reset, so that the analog switch 10 is open to be nonconductive and the analog switch 12 is closed to be conductive. Therefore, the flow volume control valve 1 can be controlled by the resistance of the flow volume selecting variable resistance 11. It is assumed that the volume of the constant flow in this situation is supplied as being sufficient for an inspiration volume of the patient.

Now, when the patient inspires, the inner pressure of the respiratory circuit C is made low. The pressure sensor 2 can detect the reduced inner pressure as a negative airway pressure. The second set voltage V2 of the second voltage setter 6 is selected as corresponding to a predetermined value, e.g., "5 liter per minute". When this negative airway pressure is lower than "0 cm H2O" corresponding to the value of the second voltage V2, the output of the comparator 4 is made low to thereby reset the flip/flop 8. Therefore, the analog switch 10 is turned off while the analog switch 12 is turned on. Here, the volume of the constant flow P in the respiratory circuit C is increased up to a volume selected by the flow volume selecting rariable resistance 11.

On the other hand, when the patient expires, the inner pressure of the respiratory circuit C is increased. The pressure sensor 2 can detect the increased inner pressure as a positive airway pressure. The third voltage V3 of the third voltage setter 7 is selected as corresponding to a predetermined value, e.g., "3.5 cm H2O". When the positive airway pressure exceeds "3.5 cm H2O" corresponding to the third voltage V3 of the third voltage setter 7, the output of the comparator 5 is made low, so that the flip/flop 8 is set. Hence, the analog switch 10 is turned on while the analog switch 12 is turned off. Therefore, the volume of the constant flow P in the respiratory circuit C is reduced to a predetermined value, e.g., "5 liter per minute" corresponding to the first voltage V1.

Thus, according to the changes in volume during the patient's inspiration and expiration the above operations are repeated.

Thus, in the preferred embodiment of the present invention, the volume of the constant flow is controlled so that when a negative airway pressure is generated by the patient's inspiration and, namely, the inner pressure of the respiratory circuit is lowered, the constant flow volume is increased to return the initial constant flow volume and that when a positive airway pressure is caused by the patient's expiration and, namely, the inner resistance of the respiratory circuit exceeds a predetermined value, the constant flow volume is reduced so that the resistance to the patient's own respiration is lowered. The inner pressure of the respiratory circuit can fall within a predetermined range, so that an appropriate volume of the air containing O2 can be continuously supplied reversely proportional to the patient's own respiration. Further, it is possible to minimize the amount of air used.

It may be evident to one of ordinary skill in the art that a microcomputer can be provided for controlling the volume of the constant flow P according to the changes in the inner pressure of the respiratory circuit C in yet another embodiment of the present invention.

While only certain embodiments of the present invention have been described, it will be apparent to those skilled in the art that various changes and modifications may be made therein without departing from the spirit and scope of the present invention as claimed.

What is claimed is:

1. An artificial respiration ventilator for controlling the volume of continuous air flow passing into a patient's lungs comprising:
respiratory circuit means for conducting a continuous air flow from a source to a patient's lungs during inhalation and exhalation phases of a respiratory cycle;
sensing means for sensing a generation of positive and negative airway pressures in the respiratory circuit means caused by inhalation and exhalation efforts;
means for generating a plurality of threshold signals corresponding to predetermined positive and negative airway pressure threshold value
threshold detection means, responsive to said sensing means, for ascertaining when said sensed positive and negative airway pressures exceed said threshold values;
means for generating a plurality of reference input signals corresponding to a plurality of air volume flow rate values;
switching means, responsive to said threshold detection means, for choosing one from a plurality of reference input signals when one of the plurality of threshold values is exceeded; and
air volume flow rate adjusting means, responsive to the output of said switching means, for continuously and instantaneously adjusting the air volume flow rate through the respiratory circuit means in accordance with the reference input value chosen by said switching means such that the continuous air flow through substantially inversely proportioned to the sensed positive and negative airway pressures.

2. The artificial respirator ventilator of claim 1, wherein said sensing means senses the positive and negative airway pressures by referring to a change in inner pressure of said respiratory circuit means.

3. The artificial respiration ventilator of claim 1 wherein said air volume flow rate adjusting means increases the air volume flow rate through the respiratory circuit means if the sensed negative airway pressure exceeds a first threshold value and wherein said air volume flow rate adjusting means further decreases the air volume flow rate through the respiratory circuit means if the sensed positive airway pressure exceeds a second threshold value.

* * * * *